(12) United States Patent
Petrovic et al.

(10) Patent No.: US 7,087,069 B2
(45) Date of Patent: Aug. 8, 2006

(54) VASCULAR ANCHORING DEVICE

(76) Inventors: Dragan Petrovic, Füchselhofgasse 7/25, A-1120, Vienna (AT); Aleksandar Vujanic, Brigittenauer Lände 160-162/4/8, A-1200, Vienna (AT); Werner Brenner, Friedlgasse 5, A-1190, Vienna (AT); Ali H. M. Hassan, Brünnerstrasse 107-109/2/6, A-1210, Vienna (AT)

( * ) Notice: Subject to any disclaimer, the term of this patent is extended or adjusted under 35 U.S.C. 154(b) by 652 days.

(21) Appl. No.: 10/333,832

(22) PCT Filed: Jul. 24, 2001

(86) PCT No.: PCT/AT01/00253

§ 371 (c)(1),
(2), (4) Date: Mar. 26, 2003

(87) PCT Pub. No.: WO02/07645

PCT Pub. Date: Jan. 31, 2002

(65) Prior Publication Data
US 2004/0039405 A1 Feb. 26, 2004

(30) Foreign Application Priority Data
Jul. 25, 2000 (AU) .............................. A 1305/2000

(51) Int. Cl.
*A61B 17/00* (2006.01)
*A61M 1/00* (2006.01)
*A61M 25/00* (2006.01)

(52) U.S. Cl. ...................... 606/200; 606/113; 606/114; 606/127; 606/159

(58) Field of Classification Search ................ 606/200, 606/113–114, 127, 159
See application file for complete search history.

(56) References Cited

FOREIGN PATENT DOCUMENTS

| FR | 2 580 504 | 10/1986 |
| FR | 2 666 980 | 3/1992 |
| WO | WO 00/07521 | 2/2000 |

*Primary Examiner*—Anhtuan T. Nguyen
*Assistant Examiner*—M. Thomas Andersen
(74) *Attorney, Agent, or Firm*—Chapman and Cutler LLP

(57) ABSTRACT

In a vascular anchoring device intended to be introduced into a blood vessel by a catheter and including braces (2) that are expandable in the radial direction, the anchoring device is formed by a substantially hollow-cylindrical part (1) including axially extending braces (2) departing from an end side, and a locking member (3) coaxially guided within the hollow-cylindrical part (1) along a guide wire (4) of the catheter. The locking member (3) carries at least one ramp surface (9) on its end facing the braces (2), which ramp surface causes the braces (2) to expand by an axial displacement relative to the braces (2), and at least one stop (10) cooperating with the hollow-cylindrical part (1) in the expanded position. The guide wire (4) carries a further stop (7) which cooperates with a counter stop surface (8) of the locking member (3), upon displacement of the guide wire (4).

36 Claims, 1 Drawing Sheet

VASCULAR ANCHORING DEVICE

This application is a 371 of PCT/AT01/00253 filed Jul. 24, 2001.

BACKGROUND OF INVENTION

1. Field of Invention

The invention relates to a vascular anchoring device intended to be introduced into a blood vessel by a catheter and including braces that are expandable in the radial direction.

2. Background Information

In order to position intravascular surgical tools or treatment aids, catheters are usually employed, which enable the expansion of blood vessels by arranging balloons of a balloon catheter or the insertion of stents or surgical tools for operative interventions into blood vessels. As a rule, the catheter is introduced via a blood vessel such as, for instance, the femoral artery or the brachial artery in order to render feasible the required treatment on the respective site. Such an intervention, however, always entails the risk of particles and, in particular, plaque particles being released from the vessel wall into the bloodstream, thus causing damage and, in particular, embolisms and hence an interruption or throttling of the blood supply to the target tissue. It has, therefore, been already suggested in this context to use filter systems that are capable of capturing the particles released during an intervention. Known filtering systems as are described, for instance, in U.S. Pat. No. 5,300,086 comprise braces which are expandable in the radial direction and between which a filter material can be tentered radially. In that known device, the braces are designed to be biased in the radial direction and maintained in the folded position by a cladding hose which is introduced together with the guide wire and the filter. By retracting the cladding hose, it is subsequently feasible to move the braces outwards under the biasing force. When fixing such braces in a blood vessel, the guide wire is, however, no longer freely movable and, in particular, no longer movable in the axial direction beyond the site on which the radially expandable braces are in contact with the vessel wall. The bracing force is limited by the elastic prestress of the braces. In order to retract or fold these radially expanded braces, a hose-like applicator can again be lapped over the braces to effect their inward movement against the biasing force or the spring force of the braces, respectively. While the braces are opened by a tensile movement, their closure is effected by a thrust movement of the actuation member in the opposite direction.

From FR-2 580 504 A, a device for positioning an intravascular filter is, moreover, known. In that device, a blood filter capable of being inserted by means of a catheter and a guide wire and reversibly expanded by means of an inflatable balloon is described, which can be anchored within a vein. The blood filter is comprised of several flexible arms.

DESCRIPTION

The invention aims to provide a retractable vascular anchoring device of the initially defined kind, which enables both opening and closing each by a tensile movement in the same direction, and which further ensures as free a movability of the guide wire as possible beyond the anchoring site after a defined outward movement and anchorage of the braces.

To solve this object, the anchoring device according to the invention essentially consists in that the anchoring device comprises a substantially hollow-cylindrical part including axially extending braces departing from an end side, and a locking member coaxially guided within the hollow-cylindrical part along a guide wire of the catheter, that the locking member carries at least one ramp surface on its end facing the braces, which ramp surface causes the braces to expand by an axial displacement relative to the braces, and at least one stop cooperating with the hollow-cylindrical part in the expanded position, and that the guide wire carries a further stop which cooperates with a counter stop surface of the locking member, or a stop surface of the hollow-cylindrical part, upon displacement of the guide wire. Due to the fact that the anchoring device comprises a substantially hollow-cylindrical part including axially extending braces departing from an end side, and a locking member coaxially guided within the hollow-cylindrical part along a guide wire of the catheter, it has become feasible to provide an outward movement of the braces through a relative displacement of the locking member relative to the part carrying the braces, for instance by simply retracting the guide wire, to which end the configuration is devised such that the locking member which is axially displaceable along the guide wire carries at least one ramp surface on its end facing the braces, which ramp surface causes the braces to expand due to an axial displacement relative to the braces. To this end, it is merely required to appropriately secure the hollow-cylindrical part carrying the braces against displacement, which is readily feasible by the aid of an applicator in the form of a hose slipped over the guide wire. By retracting the guide wire, a stop provided on the guide wire is brought into active connection with the locking member and displaces the locking member relative to the hollow-cylindrical part, thus causing the braces to expand on account of the ramp surfaces. When kinematically reversing this movement, a stop of the guide wire is able to cooperate with the structural component carrying the braces, while the applicator cooperates with the locking member. By the locking member carrying at least one stop cooperating with the hollow-cylindrical part in the expanded position, the locking member can be retracted into the respective position in which a defined expanded position is assumed by the braces and locking of the expanded position is simultaneously ensured by the stop preventing a new displacement of the locking member-opposite to the direction of displacement of the guide wire. Such stops can be formed by surfaces of any desired shape, which cooperate in the axial direction such as, e.g., grooves, holes, tongues or the like. Under those circumstances, automatic locking is, thus, ensured with the guide wire retaining its free axial displaceability at least to the extent that the stop of the guide wire will not collide with the locking member or the structural component carrying the braces. For the automatic closure of the expandable braces and the detachment of the anchorage, the locking member can subsequently be retracted beyond the locking position by newly applying the hose-like applicator through movement in the same direction, which will again result in the automatic inward movement of the substantially axially extending, yet radially outwardly moved braces, due to the elasticity of the hollow-cylindrical part. The inward movement in a particularly advantageous manner can be facilitated in that, as in correspondence with a preferred embodiment of the invention, the braces are encompassed by a ring of elastomeric material. The expansion or extension of the braces in the radial direction can be promoted by designing the ramp surfaces as wedge or conical surfaces.

Such a configuration, therefore, provides a kinematics by which an expansion of the braces is initially effected via the ramp surfaces, which may be designed as wedge, annular bead or conical surfaces, for instance by the retraction of the guide wire under the collision of the guide wire stop with the locking member, and the inward movement of the braces is subsequently enabled by further retraction of the guide wire, i.e. movement in the same sense, while entraining the locking member.

The anchoring device can be employed for any desired application and, while fully maintaining the functionality of the guide wire, offers the essential advantage of providing a defined anchoring site relative to which, or on which, further auxiliary means can be arranged. Thus, it is feasible to introduce, along the guide wire, to the treatment site the balloons of a balloon catheter or stents or surgical instruments required for the intravascular intervention, wherein it is, of course, also feasible in a particularly simple manner to use the anchoring device for tentering a filter.

Additional treatment aids such as, for instance, means for dosing in drugs can be readily coupled with the anchoring device, to which end the configuration advantageously is devised such that the end of the hollow-cylindrical part facing away from the braces carries coupling members and, in particular, magnetic or latchable coupling members. Such coupling members which enable detachable coupling and hence uncoupling also allow for the appropriate dislocation of the anchor by means of suitable coupleable applicators with the braces retracted.

In order to facilitate the introduction of the braces and the withdrawal of the newly retracted braces, the configuration preferably is devised such that the braces are designed as fingers following the hollow-cylindrical part and bent or curved in the axial direction.

Overall, a positionable and detachable vascular anchoring device is, thus, provided, which can be introduced and fixed on the desired site by particularly simple means, its installation and removal being, for instance, feasible by a simple tensile movement without reversal of the direction of movement of the guide wire. At the same time, as large a movability and displaceability of the guide wire as possible are safeguarded for subsequent operations in a given position of the anchoring device, thus substantially facilitating intravascular interventions. Intravascular treatments can be carried out in blood vessels according to standards via balloons and/or stents or the like, which are introduced by means of a guide wire, while the capture of particles released during an intervention is simultaneously feasible when using the anchoring device as a filter. The anchoring device in a particularly advantageous manner may be made of materials which are visible under X-rays and, for instance, comprise metallic filter fingers so as to enable the safe pursuit of the respective position.

BRIEF DESCRIPTION OF DRAWINGS

In the following, the invention will be explained in more detail by way of an exemplary embodiment schematically illustrated in the drawing. Therein.

DETAILED DESCRIPTION OF DRAWINGS

Figure 1:
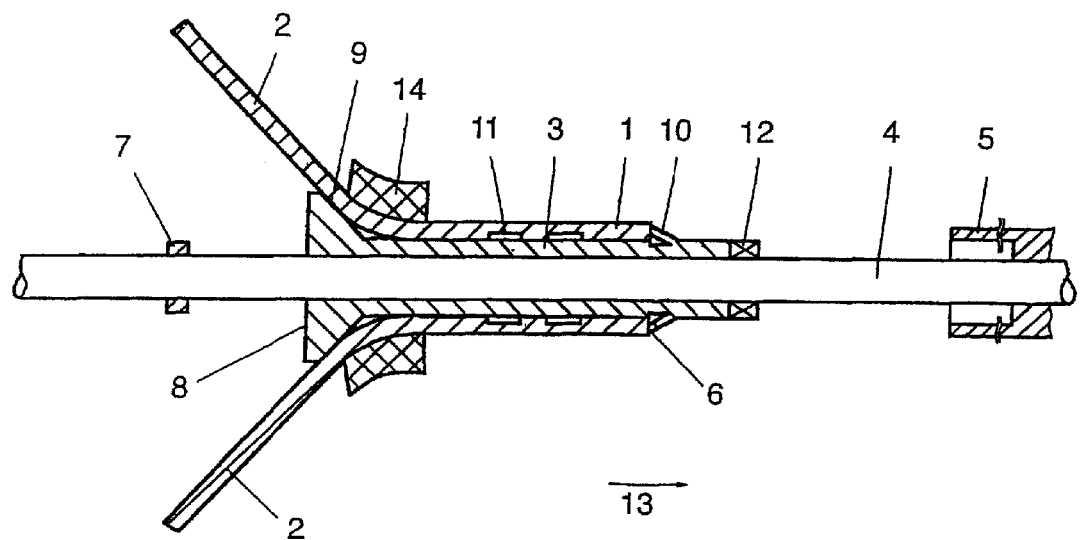
FIG. 1 is a cross-sectional view through the anchoring device according to the invention with extended braces.

FIG. 1 depicts a substantially cylindrical base body 1, which comprises braces 2 provided on its end side. The substantially cylindrical base body 1, together with a locking member 3, is each guided concentrically with a guide wire 4 so as to be displaceable in the axial direction of the same. Its introduction is effected via an applicator schematically indicated at 5, which is slipped over the guide wire 4 in the manner of a flexible hose, thus cooperating with the end face 6 of the hollow-cylindrical part 1, that faces away from the braces 2. In the folded position of the braces, the hollow-cylindrical part 1 together with the braces can, thus, be placed into the respective position by means of the applicator 5. By retracting the guide wire 4, it is feasible to bring into active connection with the end face 8, or a stop of the locking member 3 projecting in the axial direction, a stop 7 provided on the guide wire, thus causing the locking part 3 to be retracted under expansion of the braces 2. The expansion of the braces 2 is effected via ramp surfaces 9 of the locking member, which are designed as conical surfaces. The locking member 3 carries at least one elastically unfoldable or deformable stop 10, which is able to cooperate with the hollow-cylindrical part 1 in different positions. To this end, annular grooves 11 are provided, whereby the elastically deformable stop 10 is able to latch in one of these annular grooves 11, thus causing the braces 2 to assume a defined expanded position. The annular grooves 11 may be replaced with openings such as, e.g., slots or holes, wherein, with the kinematics reversed, annular grooves, slits or holes provided in the locking member 3 are naturally able to cooperate with accordingly elastically deformable stops 10 provided on the hollow-cylindrical part 1. With the braces completely extended, the unfoldable stop 10 illustrated engages from behind the end face 6 of the hollow-cylindrical part, that faces away from the braces, locking being feasible in different expanded positions of the braces 2. After the braces 2 have been locked and extended, the applicator 5 can be removed again and the guide wire 4 can be displaced in the axial direction, which displacement is limited merely by the fact that the stop 7 of the guide wire 4 cannot be retracted beyond the stop 8 of the locking member 3 upon positioning of the anchoring device.

On its end facing away from the braces, the locking part 3 may carry coupling members schematically indicated at 12, to which additional means can be coupled.

Figure 2:
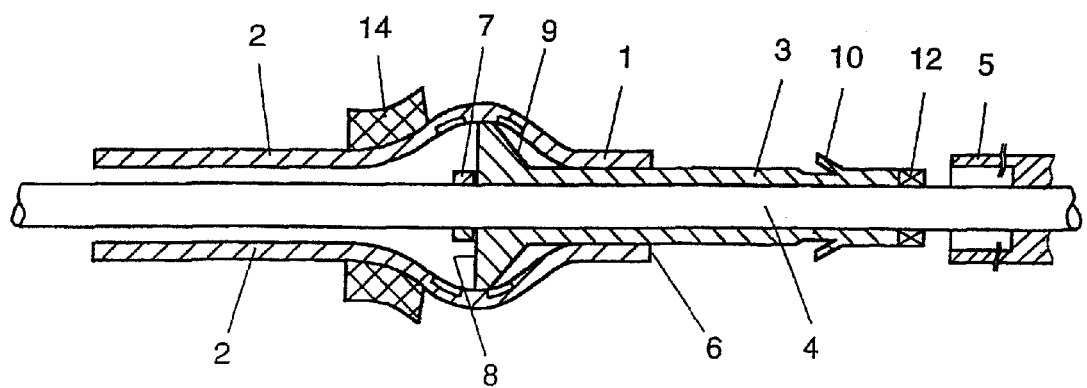
FIG. 2 is a cross-sectional view analogous to FIG. 1 with folded braces.

In order to unlock the anchoring device, the applicator 5 can be newly slipped on and cooperate with the end face 6 of the hollow-cylindrical part. As the guide wire 4 is subsequently pulled back in the sense of arrow 13, the part carrying the ramp surfaces 9 enters the hollow-cylindrical part 1 under elastic deformation of the latter, thus causing the braces 2 to again move radially inwards and get out of engagement with the vessel wall. This inward movement can be promoted by an elastomeric ring 14, which is apparent, in particular, from FIG. 2. In that inwardly folded position of the braces 2, it is again feasible to completely retract the anchoring device without entailing any risk of injury to the blood vessel.

The braces 2 may be connected with a filter not illustrated in the Figures, which can be tentered over the total cross section of the blood vessel with the braces being positioned as illustrated in FIG. 1.

The invention claimed is:

1. A vascular anchoring device intended to be introduced into a blood vessel by a catheter and including braces that are expandable in a radial direction, wherein the anchoring device comprises a substantially hollow-cylindrical part (1) including axially extending braces (2) extending from an end side of said hollow-cylindrical part, and a locking member (3) coaxially guided within the hollow-cylindrical part (1) along a guide wire (4) of the catheter, and wherein the locking member (3) carries at least one ramp surface (9) on an end of said locking member (3) facing the braces (2), which ramp surface causes the braces (2) to expand by an axial displacement relative to the braces (2), and at least one stop (10) cooperating with the hollow-cylindrical part (1) when the braces (2) are in an expanded position, and the guide wire (4) carries a further stop (7) which cooperates with a counter stop surface (8) of the locking member (3), upon displacement of the guide wire (4).

2. A vascular anchoring device according to claim 1, wherein the ramp surface (9) is designed as a wedge surface.

3. A vascular anchoring device according to claim 1, wherein the ramp surface (9) is designed as an annular bead surface.

4. A vascular anchoring device according to claim 1, wherein the ramp surface (9) is designed as a conical surface.

5. A vascular anchoring device according to claim 1, wherein the braces (2) are encompassed by a ring (14) of elastomeric material.

6. A vascular anchoring device according to claim 2, wherein the braces (2) are encompassed by a ring (14) of elastomeric material.

7. A vascular anchoring device according to claim 3, wherein the braces (2) are encompassed by a ring (14) of elastomeric material.

8. A vascular anchoring device according to claim 4, wherein the braces (2) are encompassed by a ring (14) of elastomeric material.

9. A vascular anchoring device according to claim 1, wherein an end of the hollow-cylindrical part (1) facing away from the braces (2) carries coupling members (12).

10. A vascular anchoring device according to claim 2, wherein an end of the hollow-cylindrical part (1) facing away from the braces (2) carries coupling members (12).

11. A vascular anchoring device according to claim 3, wherein an end of the hollow-cylindrical part (1) facing away from the braces (2) carries coupling members (12).

12. A vascular anchoring device according to claim 4, wherein an end of the hollow-cylindrical part (1) facing away from the braces (2) carries coupling members (12).

13. A vascular anchoring device according to claim 5, wherein an end of the hollow-cylindrical part (1) facing away from the braces (2) carries coupling members (12).

14. A vascular anchoring device according to claim 1, wherein an end of the hollow-cylindrical part (1) facing away from the braces (2) carries magnetic or latchable coupling members (12).

15. A vascular anchoring device according to claim 2, wherein an end of the hollow-cylindrical part (1) facing away from the braces (2) carries magnetic or latchable coupling members (12).

16. A vascular anchoring device according to claim 3, wherein an end of the hollow-cylindrical part (1) facing away from the braces (2) carries magnetic or latchable coupling members (12).

17. A vascular anchoring device according to claim 4, wherein an end of the hollow-cylindrical part (1) facing away from the braces (2) carries magnetic or latchable coupling members (12).

18. A vascular anchoring device according to claim 5, wherein an end of the hollow-cylindrical part (1) facing away from the braces (2) carries magnetic or latchable coupling members (12).

19. A vascular anchoring device according to claim 1, wherein a filter is connected with the braces (2) and is capable of being tentered over a cross section of the blood vessel.

20. A vascular anchoring device according to claim 2, wherein a filter is connected with the braces (2) and is capable of being tentered over a cross section of the blood vessel.

21. A vascular anchoring device according to claim 3, wherein a filter is connected with the braces (2) and is capable of being tentered over a cross section of the blood vessel.

22. A vascular anchoring device according to claim 4, wherein a filter is connected with the braces (2) and is capable of being tentered over a cross section of the blood vessel.

23. A vascular anchoring device according to claim 5, wherein a filter is connected with the braces (2) and is capable of being tentered over a cross section of the blood vessel.

24. A vascular anchoring device according to claim 6, wherein a filter is connected with the braces (2) and is capable of being tentered over a cross section of the blood vessel.

25. A vascular anchoring device according to claim 7, wherein a filter is connected with the braces (2) and is capable of being tentered over a cross section of the blood vessel.

26. A vascular anchoring device according to claim 8, wherein a filter is connected with the braces (2) and is capable of being tentered over a cross section of the blood vessel.

27. A vascular anchoring device according to claim 1, wherein the braces (2) are designed as fingers following the hollow-cylindrical part (1) and are bent or curved in an axial direction.

28. A vascular anchoring device according to claim 2, wherein the braces (2) are designed as fingers following the hollow-cylindrical part (1) and are bent or curved in an axial direction.

29. A vascular anchoring device according to claim 3, wherein the braces (2) are designed as fingers following the hollow-cylindrical part (1) and are bent or curved in an axial direction.

30. A vascular anchoring device according to claim 4, wherein the braces (2) are designed as fingers following the hollow-cylindrical part (1) and are bent or curved in an axial direction.

31. A vascular anchoring device according to claim 5, wherein the braces (2) are designed as fingers following the hollow-cylindrical part (1) and are bent or curved in an axial direction.

32. A vascular anchoring device according to claim 6, wherein the braces (2) are designed as fingers following the hollow-cylindrical part (1) and are bent or curved in an axial direction.

33. A vascular anchoring device according to claim 7, wherein the braces (2) are designed as fingers following the hollow-cylindrical part (1) and are bent or curved in an axial direction.

34. A vascular anchoring device according to claim 8, wherein the braces (2) are designed as fingers following the hollow-cylindrical part (1) and are bent or curved in an axial direction.

35. A vascular anchoring device according to claim 9, wherein the braces (2) are designed as fingers following the hollow-cylindrical part (1) and are bent or curved in an axial direction.

36. A vascular anchoring device according to claim 19, wherein the braces (2) are designed as fingers following the hollow-cylindrical part (1) and are bent or curved in an axial direction.

* * * * *